United States Patent [19]

Dave

[11] Patent Number: 5,580,988
[45] Date of Patent: Dec. 3, 1996

[54] SUBSTITUTED AZETIDINES AND PROCESSES OF USING THEM

[75] Inventor: Paritosh R. Dave, Bridgewater, N.J.

[73] Assignee: The United States of America as represented by the Secretary of the Army, Washington, D.C.

[21] Appl. No.: 441,511

[22] Filed: May 15, 1995

[51] Int. Cl.$^6$ .................................................. C07D 205/04
[52] U.S. Cl. ............................................................ 548/953
[58] Field of Search .............................................. 548/953

[56] References Cited

U.S. PATENT DOCUMENTS 5,476,951  12/1995  Dave et al. ............................... 548/953

*Primary Examiner*—Jacqueline Haley
*Attorney, Agent, or Firm*—Edward Goldberg; Michael C. Sachs; John E. Callaghan

[57] ABSTRACT

New N-nitro, 3 substituted azetidine compounds are disclosed and these are used in processes to prepare TNAZ.

2 Claims, 2 Drawing Sheets

5,580,988

SUBSTITUTED AZETIDINES AND PROCESSES OF USING THEM

STATEMENT OF GOVERNMENT INTEREST

The invention described herein may be manufactured, used or licensed by or for the United States Government for governmental purposes without payment to the inventor(s) of any royalties.

STATEMENT OF RELATED APPLICATIONS

This application is related to the U.S. Patent applications described below; the applications have been filed on the same date as this application. The applications are:

| | | | |
|---|---|---|---|
| DAR 4-94A | S.N. 08/440,947 | May 15, 1995 | pending |
| DAR 4-94B | S.N. 08/440,946 | May 15, 1995 | pending |
| DAR 4-94C | S.N. 08/440,945 | May 15, 1996 | pending |
| DAR 4-94E | S.N. 08,441,512 | May 15, 1995 | pending |

BACKGROUND OF INVENTION

Azetidines are four member ring compounds having one nitrogen and three carbon atoms. As a four member ring, there is ring strain which leads to difficulties in preparation of the azetidines and more difficulties in substitutions and modifications of azetidines. The compounds are of importance as intermediates leading to 1,3,3 trinitroazetidine, TNAZ, an energetic material that can be melt cast or press loaded into articles for use as an explosive or propellant. Other azetidine compounds are biologically active and have pharmalogical properties. A major obstacle has been that the substituted azetidines have been impossible to prepare or the synthesis routes can not provide adequate quantities at a reasonable cost. The present invention is directed to new azetidine compounds and new processes which use the compounds.

SUMMARY OF INVENTION

In the related applications, novel methods for preparations of azetidines are disclosed. This application concerns several new azetidine compounds and additional processes to prepare TNAZ. It includes new halogen substituted azetidines and azetidines having ketone, acyloxy and hydroxy substituents in the 3-position. The Figures show the preparation of the substitued azetidines and the use of these azetidines to make TNAZ.

DETAILED DESCRIPTION OF THE INVENTION

The azetidines of this invention are four member heterocycles which have substituents on the aza nitrogen and the 3-position of the ring. The particular classes of compounds are those with N-nitro and N-acyl substituents. The acyl group includes the haloacyl as well as carboxyl groups. As for the 3-position, the substituent may be a halo, keto, hydroxy, or oximido group. The substituted compounds are able to participate in further substitutions and reactions without breakdown of the four member ring. One particular class of compounds are the 3-keto azetidines having an electron withdrawing group at the aza position. These are now available by this invention.

An important process of the invention is the conversion of the azetidines to TNAZ by several alternate routes. One route uses the N-acyl, 3-keto-azetidine and another route uses the N-nitro, 3-keto-azetidine. Another aspect of the invention is that the new compounds are precursors to other materials that are valuable such as azabicylobutane and N-triflurotacetyl, 3-(meta-trifloromethyl) phenoxyazetidine.

Figure 1:
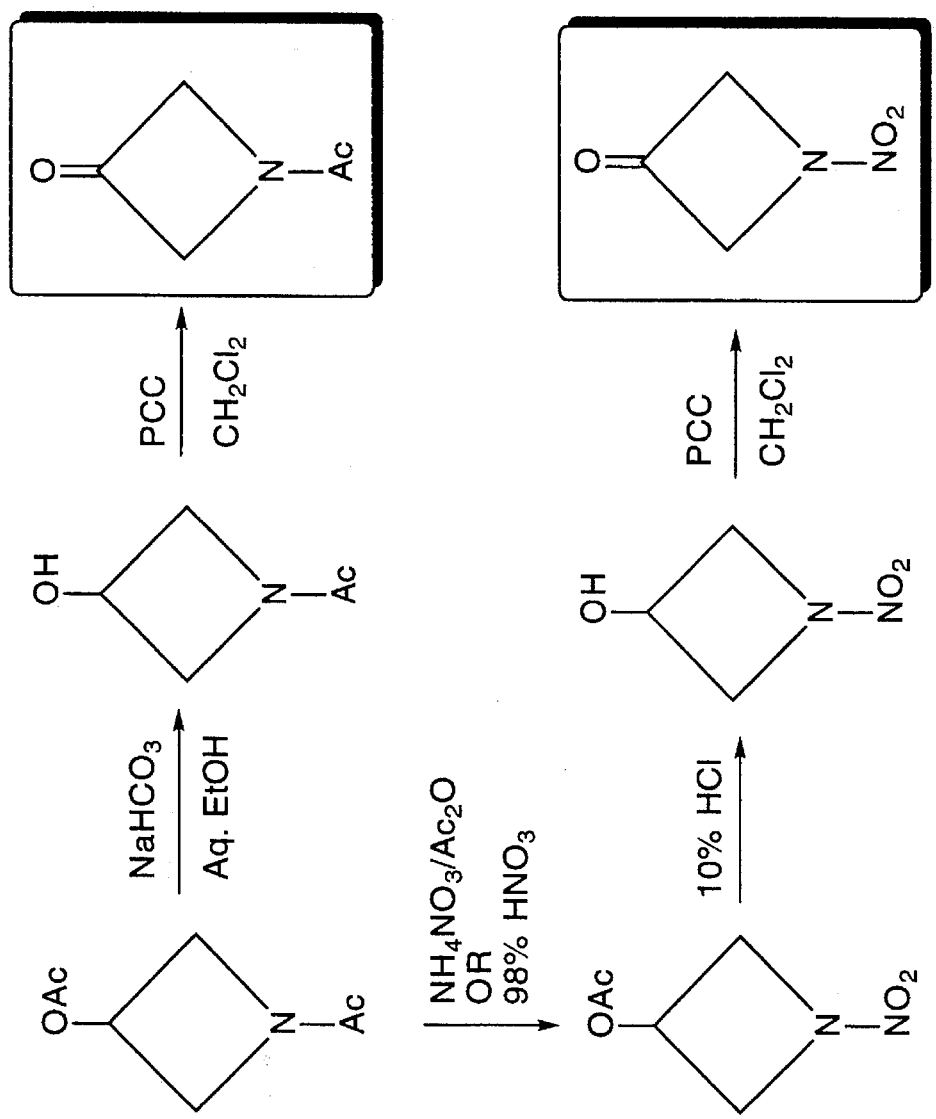
FIG. 1 shows the hydrolysis of N-acetyl, 3-acetoxyazetidine with alkaline aqueous ethanol to convert the acetoxy to the 3-hydroxy compound. This compound is nitrated to form the N-nitroazetidine.

The substituted azetidines are generally prepared from starting materials that are prepared by acylative dealkylation of N-tertiary butyl azetidine through reacting the azetidine with a catalytic amount of a non-protic Lewis acid and in the presence of an electrophillic compound. The tertiary butyl is split out and the substituent subtituent attaches at the aza nitrogen. The co-pending application Ser. No. 08/440,945, describes these reactions. For the present invention it is preferred to start with the N-acetyl, 3-acetoxyazetidine, the acetyl functions are recognized in the field as good starting places for preparation of other derivatives of the parent compound. As shown in FIG. 1, the compound can be hydrolysed with alkaline aqueous ethanol to convert the 3-acetoxy to the 3-hydroxy compound. Conventional oxidixing agents such as pyridinium chlorochromate will oxidize the hydroxyl group to the ketone and the ring stays intact. The ketone is alternatively known as the azetidinone. The procedure of substitution is general for the N-acetyl, 3-substituted azetidines.

The N-nitro compounds can also be prepared from the N-acetyl, 3-acetoxy-azetidine. The N-acetyl is converted to the N-nitro by reacting the parent compound with a nitrating agent such as 98% nitric acid or ammonium nitrate in acetic anhydride. The 3-acetoxy group can be hydrolysed to the 3-hydroxy group by aqueous hydrochloric acid. The N-nitro, 3-hydroxyl azetidine can be oxidized to the 3-ketone without ring cleavage. In the example, pyridinium chloro chromate is illustrated as the oxidizing agent.

For the N-trihaloacyl, 3-hydroxy azetidines, the most efficient procedure is to react N-tertiarybutyl, 3hydroxyazetidine with a catlytic amount of a non-protic Lewis acid in trifluoro acetic anhydride, and then neutralize it in aqueous sodium hydrogen carbonate. This directly produces the N-trifluoroacetyl, 3-hydroxyazetidine. Similarly, the N-acyl, 3-haloazetidines can be prepared from the N-tertiarybutyl, 3-haloazetidine by acylative dealkylation in acetic anhydride with a catalytic amount of a non-protic Lewis acid. The preparation of the chloro substituted compound is typical.

In these reactions, the formation of the desired compounds can be followed by NMR techniques. The following illustrates how the reactions were followed and the identification of the individual compounds by this technique. The data presents the shifts for the respective $^1$H NMR and $^{13}$C NMR:

| | |
|---|---|
| N-acetyl, 3-keto azetidine | $^1$H 4.8(s,2H), 4.9(s,3H), 2.1(2,3H) (CDCl$_3$) $^{13}$C 20.8; 70.4; 71.4; 194.8 |
| N-nitro, 3-acetoxy azetidine | $^1$H 2.1(s,3H), 4.3–4.75(m,4H), 5.1(s,1H) (CDCl$_3$) $^{13}$C 20.9; 60.6: 63.8; 170.6 |

-continued

| | |
|---|---|
| N-nitro, 3-hydroxy azetidine | $^1$H 3.8(s,1H), 4.2(m,2H), 4.5(m,3H) (CDCl$_3$) $^{13}$C 58.7, 66.8 |
| N-acetyl, 3-chloro azetidine | $^1$H 2.1(s,3H), 3.5(m,2H), 3.9(m,2H), 4.5(m,1H) (CDCl$_3$) $^{13}$C not presented for this compound |

Figure 2:
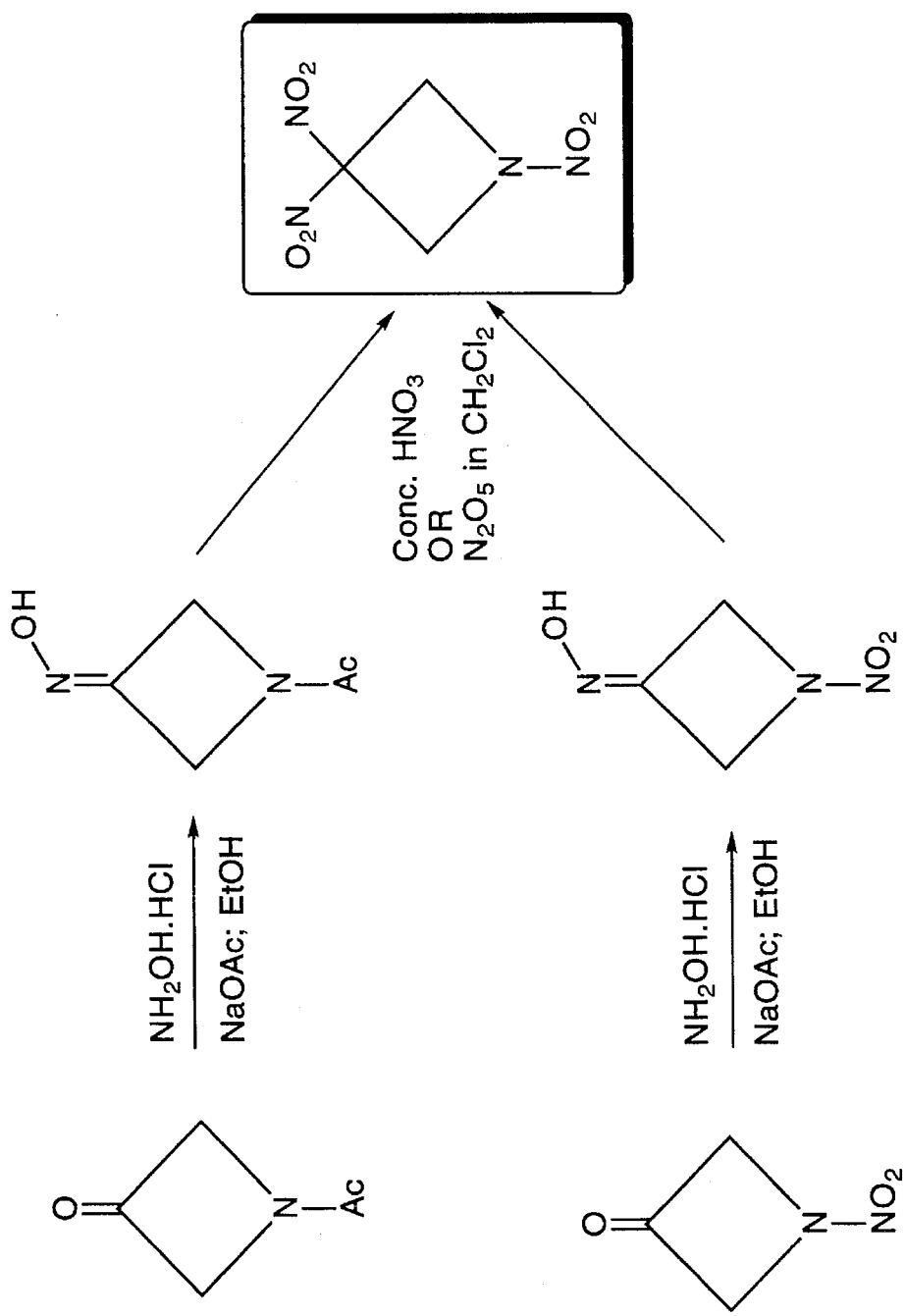
FIG. 2 shows the conversion of N-acetyl, 3-ketoazetidine to the N-acetyl, 3-oximidoazetidine followed by reaction with nitric acid or nitrogen pentoxide to produce TNAZ.

An important use of these azetidines is illustrated in FIG. 2. These will produce TNAZ. The upper process shows a first step which is the conversion of the N-acetyl, 3-ketoazetidine to the N-acetyl, 3-oximidoazetidine. The ketone is converted to the oxime. The N-acetyl, 3-oximidoazetidine is reacted with concentrated nitric acid or nitrogen pentoxide to produce TNAZ. The advantage of the process is that it uses an oxime with the nitrating system that will add all of the nitro groups in the final step. The ease of removal of the acetyl group is an important advantage in this nitration.

In FIG. 2, the lower process to produce TNAZ is shown starting with the N-nitro, 3-ketoazetidine. It is converted to the N-nitro, 3-oximidoazetidine which is then nitrated to add the two nitro groups to the ring and form TNAZ. The reagents for the reaction steps are shown in the Figures.

It can be seen that the compounds and processes are capable of wide variation and modification. The new compounds and the efficiencies acheived with the invention are important contributions. However, while the preferred embodiments have been described with reference to particular features, sequences of steps, functional groups and other ring substituents and proportions, it is intended that this invention shall cover such structures, applications and uses as those in the field would deem equivalents.

I claim:

1. A compound selected from the group of N-nitro, 3-acyloxyazetidines and N-nitro, 3-hydroxyazetidine.

2. A compound according to claim 1 selected from N-nitro, 3-hydroxyazetidine and N-nitro, 3-acetoxyazetidine.

* * * * *